(12) United States Patent
Park

(10) Patent No.: US 6,936,557 B2
(45) Date of Patent: Aug. 30, 2005

(54) MINERAL COMPOSITION AND METHOD FOR MANUFACTURING THE SAME

(76) Inventor: Yong-Jin Park, Baeknam Bldg., 988, Dunsan-dong, Seo-ku, Daejeon-city (KR)

(*) Notice: Subject to any disclaimer, the term of this patent is extended or adjusted under 35 U.S.C. 154(b) by 170 days.

(21) Appl. No.: 10/154,817

(22) Filed: May 28, 2002

(65) Prior Publication Data
US 2003/0176274 A1 Sep. 18, 2003

(30) Foreign Application Priority Data
Mar. 14, 2002 (KR) .......................... 2002-13685

(51) Int. Cl.$^7$ .......................... C30B 29/34; C04B 35/18
(52) U.S. Cl. .................. 501/86; 501/128; 501/141; 264/671; 252/587
(58) Field of Search .................. 501/86, 126, 127, 501/141, 128; 264/671; 252/587

(56) References Cited

U.S. PATENT DOCUMENTS 6,402,991 B1 * 6/2002 Itakura et al. .............. 252/500

2003/0047027 A1 * 3/2003 Sato .......................... 75/228

* cited by examiner

Primary Examiner—Karl Group
(74) Attorney, Agent, or Firm—Robert E. Bushnell, Esq.

(57) ABSTRACT

A novel multipurpose mineral composition capable of emitting a large quantity of far infrared rays, negative ions and oxygen heat is manufactured by setting up an iron railing, an iron rod and an iron plate on a brazier, placing a tinfoil on the iron plate, and layering yellow soil, kaolin, sericite, and biomineral in sequence on the tinfoil, while inserting the tinfoil between the layers, loading a pulverized elvan in the furnace, pulverizing a mixed stone including 40 wt % of germanium, 15 wt % of tourmaline, 30 wt % of zeolite, and 15 wt % of franklinite, to the particle size under about 44 μm, and loading the pulverized mixed stone in an internal furnace which is made by winding a copper plate with a tinfoil and placed on the plurality of layers of the furnace, heating the pulverized mixed stone at about 1,000° C. for about seven days into a lump, and repulverizing the lump.

20 Claims, 2 Drawing Sheets

US 6,936,557 B2

MINERAL COMPOSITION AND METHOD FOR MANUFACTURING THE SAME

CLAIM OF PRIORITY

This application makes reference to, incorporates the same herein, and claims all benefits accruing under 35 U.S.C. §119 from my application entitled NEW MULTI-PURPOSE MIRACLE POWDER AND METHOD FOR MANUFACTURING THE SAME filed with the Korean Industrial Property Office on Mar. 14, 2002 and there duly assigned Serial No. 2002-0013685.

BACKGROUND OF THE INVENTION

1. Field of the Invention

The present invention generally relates to a novel multi-purpose mineral composition emitting a large quantity of far infrared rays, negative ion and oxygen heat, and a method for manufacturing the same.

2. Description of the Related Art

It has been for a while since a variety of mineral powders capable of emitting far infrared rays and negative ions were manufactured. However, most of them use more than five different kinds of natural stones, take a very long time to heat, and require much energy and time to manufacture, which naturally made them very expensive and low in comparability.

More specifically, mineral, zeolite, green jade, amen-tree stone, and germanium were pulverized and put in the internal furnace, and zeolite was filled in-between the furnace and the internal furnace for 9-day heating before it was pulverized to manufacture the mineral powder. In another case, the internal furnace was made of amen-tree stone, and the mixed mineral powder including germanium, blackdiamond, jade, white gem and zeolite was put into the internal furnace and heated for at least nine days before the mixture was pulverized to manufacture the mineral powder emitting far infrared rays. Unfortunately however, such traditional methods proved to be problematical in many ways. First of all, the raw stone was very expensive, and many kinds of the raw stone were needed. Also, the heating time was very long requiring a great amount of time and energy, which consequently increased the manufacturing cost of the mineral powder overall.

SUMMARY OF THE INVENTION

It is, therefore, an object of the present invention to provide a novel multipurpose mineral composition with a very low price and easy access for the public, thereby contributing to human health in general.

It is also an object of the present invention to provide a method for manufacturing the novel multipurpose mineral.

In accordance with the present invention, these objects are accomplished by using a modified furnace and four kinds of natural stones that are low in price and easy to get, in which the resultant product demonstrates the similar physical properties with the traditional mineral powder despite a short heating time.

The present invention is directed to a novel mineral composition and a method for manufacturing the novel mineral composition that comprises the steps of setting up a base of a first furnace, setting up a second furnace on the base of the first furnace, loading a pulverized elvan in the first furnace, pulverizing a mixed stone comprising germanium, tourmaline, zeolite, and franklinite, loading the pulverized mixed stone in the second furnace, heating and burning the pulverized mixed stone at approximately 1,000° C. for about seven days into a lump, and repulverizing the lump.

The resultant mineral composition includes silicon, aluminum, iron, calcium, magnesium, potassium, sodium, and titanium.

It is preferred that the resultant mineral composition is as small as a particle can be passed through a number 500-mesh screen.

The pulverized mixed stones comprises about 40 wt % of the germanium, about 15 wt % of the tourmaline, about 30 wt % of said the zeolite, and about 15 wt % of the franklinite.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION OF THE PREFERRED EMBODIMENT

The present invention will be described herein below with reference to the accompanying drawings and experiments.

Figure 1:
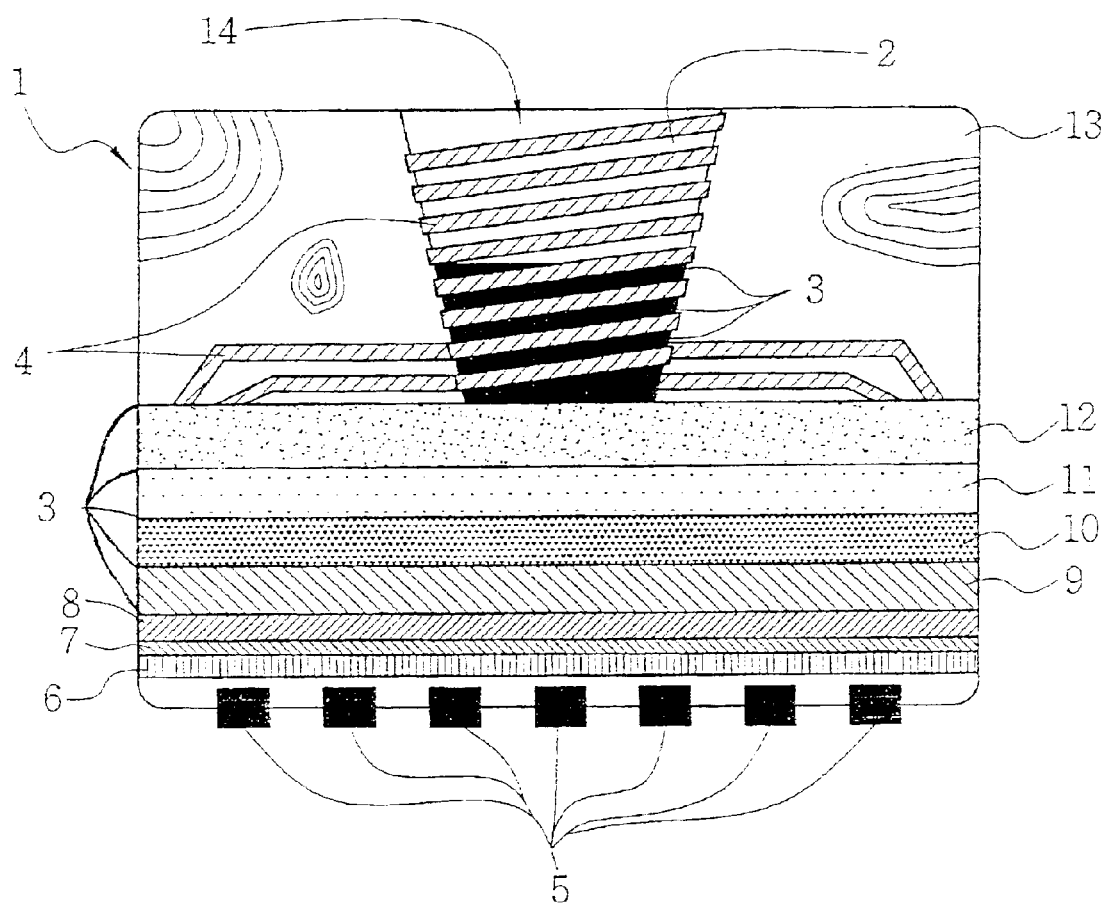
FIG. 1 is a schematic diagram illustrating a furnace for manufacturing multipurpose mineral powder according to the present invention.

Referring to FIG. 1, a furnace 1 for manufacturing a novel multipurpose mineral powder according to the present invention includes a brazier 5, a substrate formed of an iron railing 6, an iron rod 7, and an iron plate 8 on the brazier 5, a tinfoil 3 on the substrate, and a plurality of layers which includes the layers of yellow soil 9, kaolin 10, sericite 11, and biomineral 12 in sequence on the tinfoil 3. Each layer preferably has the same weight. Preferably, the base of the furnace 1 is made by inserting the tinfoil 3 on the top portion of every layer, and an internal furnace 2 is mounted on the top of the base. Then, pulverized elvan 13, the particle size of which is preferably under about 74 $\mu$m (the particle that passes a U.S. #200-mesh screen), is loaded in the furnace 1 so that the pulverized elvan surrounds the internal furnace 2. The internal furnace 2 can be prepared by wrapping a copper plate with the tinfoil 3 and by winding its external surface with a gas pipe 4 which is connected to a biomineral layer 12 and is preferably made by winding a copper wire with the tinfoil. The tinfoil 3 is also put on an inner surface and an external surface at the lower portion of the internal furnace 2.

Figure 2:
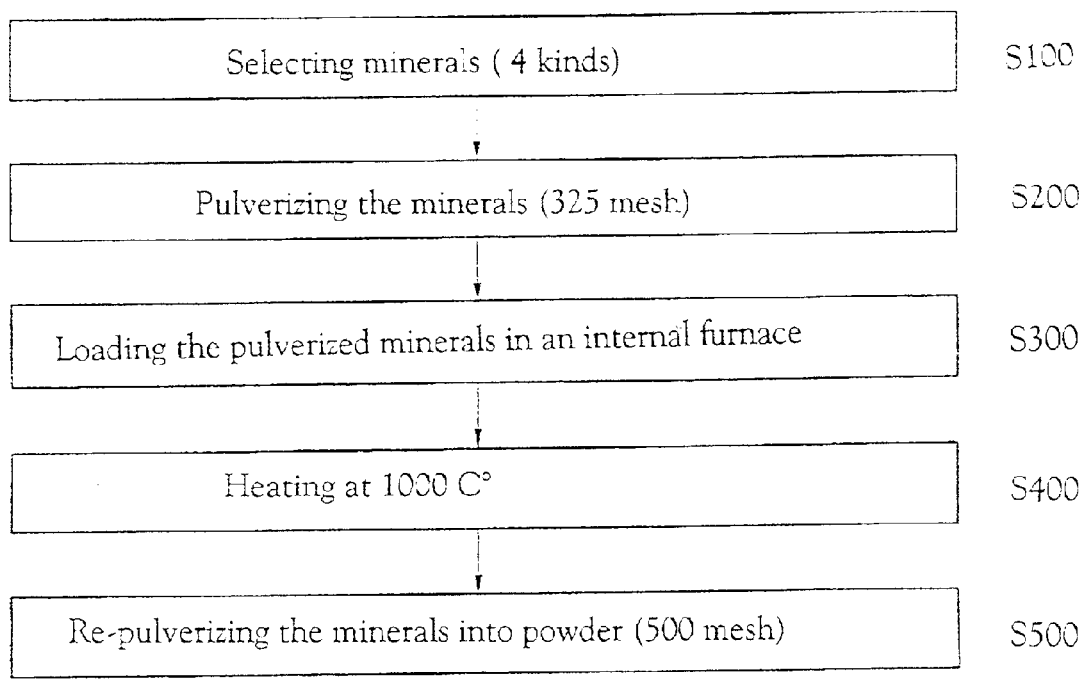
FIG. 2 is a block diagram illustrating a manufacturing process of the multipurpose mineral powder according to the present invention.

Later, the mixture of about 40 weight % (wt %) of germanium, about 15 wt % of tourmaline, about 30 wt % of zeolite and about 15 wt % of franklinite (S100 in FIG. 2) is pulverized to the particle size under about 44 $\mu$m (the particle that passes a U.S. #325-mesh screen), in a pulverizer (S200 in FIG. 2) and loaded into the internal furnace 2 (S300 in FIG. 3). This pulverized mixture is then heated approximately at 1,000° C. for about seven days through the brazier 5 (S400 in FIG. 2). Since the elvan 13 starts to heat at the initial temperature, about 1,000° C. and generates its own combustion heat by external heat, the four-component mineral powder in the internal furnace 2 experiences beat denaturation due to the high heat. In consequence, the hazardous heavy metals to the human body are burned or disappeared, and, as shown in TABLE 1, the mineral powder becomes a lump having natural mineral as main component. This lump is again pulverized until the particles of the lump can be passed through a number 500-mesh screen (S500 in FIG. 2), and the desired mineral powder is obtained therefrom.

TABLE 1

| Test Item | | Results |
|---|---|---|
| Qualitative Analysis | | Detected 8 elements: Si, Al, Fe, Ca, Mg, K, Na, Ti |
| Quantitative Analysis | $SiO_2$ | 79.3 wt % |
| | $Al_2O_3$ | 12.4 wt % |
| | $Fe_2O_3$ | 1.13 wt % |
| | CaO | 0.26 wt % |
| | MgO | 0.20 wt % |
| | $K_2O$ | 3.05 wt % |
| | $Na_2O$ | 0.65 wt % |
| | $TiO_2$ | 0.13 wt % |
| | Loss on Ignition | 2.62 wt % |
| | Ge | 1.17 mg/kg |

TABLE 1 shows the experimental results of the resultant mineral powder. The mineral powder emits a large quantity of far infrared rays, negative ions, and oxygen heat that are very good for the human body.

For a better understanding, the invention is further illustrated by the following example, which is not limitative.

EXAMPLE

As an embodiment of the present invention, a furnace 1 which is 100 meter long and 4.5 meter wide is first made. The gas braziers 5 are spaced from each other by one meter, and an iron railing 6 is erected thereon to allow the gas braziers 5 access to the furnace. On the iron railing 6, iron rods 7 are arranged one meter apart in length and width from each other. On the iron rods 7, iron plate 8 at least 0.25 cm thick is placed, and a tinfoil 3 is put on the top of the iron plate 8. Then, each of the layers of yellow soil 9, kaolin 10, sericite 11, and biomineral 12, having the tinfoil 3 between two layers, are placed in sequence to make the base of the furnace 1. Each layer is 10 ton in weight. Here, the tinfoil 3 is put on the biomineral 12 which is connected to a gas pipe 4, where the gas pipe 4 is made by winding the copper wire with the tinfoil. The gas pipe 4 winds around the internal furnace 2 whose inner wall is coated with the tinfoil. In the meantime, a pulverized elvan 13 is loaded between an inner surface of the furnace 1 and the outer surface of the internal furnace 2, and the internal furnace 2 is filled with 7,200 kg of the mixture of 40 wt % of germanium, 15 wt % of tourmaline, 30 wt % of zeolite, and 15 wt % of franklinite by pulverizing the mixture in a pulverizer to make smaller powder the size of which is below about 44 $\mu$m. Through the gas braziers 5, the mixture is heated at about 1,000° C. for about seven days and is cooled. The cooled powder is again put into the pulverizer until its size becomes as small as the powder can be passed through a number 500-mesh screen, and 7000 kg of the novel natural mineral powder is obtained. The physical properties of the powder are pretty much similar to those in TABLE 1. When the far infrared ray applicability evaluation test is conducted, the present sample emitted 63 ion/cc, and had 0.921 of emissivity at a wavelength between 5 and 20mm, and its radiation energy is $3.72 \times 10^2$ $W/m^3$.

In addition, the mineral powder of the present invention showed no clinical symptom of harming the skin when an epispastic test is performed. Further, the dermal toxicity test results assured that the mineral powder of the present invention is very safe and good for the human body, exhibiting no clinical symptom or pathological opinion related to death, when 5 g/kgB.W of the sample, the highest possible concentration for the novel mineral substance, is applied to the derma In conclusion, as shown in TABLE 1, the novel mineral powder and its manufacturing method of the present invention proved to be very advantageous not only the multipurpose mineral powder emits a large quantity of far infrared rays, negative ions and oxygen heat that are good for the human body, but also the manufacturing method saves a great deal of energy and time yet manifesting superior effect to the conventional method.

While the invention has been shown and described with reference to certain preferred embodiments thereof, it will be understood by those skilled in the art that various changes in form and details may be made therein without departing from the spirit and scope of the invention as defined by the appended claims.

What is claimed is:

1. A method for manufacturing a mineral composition, the method comprising the steps of:
   setting up a base of a first furnace;
   setting up a second furnace on said base of said first furnace;
   loading a pulverized elvan into said first furnace;
   pulverizing a mixed stone comprising germanium, tourmaline, zeolite, and franklinite;
   loading the pulverized mixed stone into said second furnace;
   heating and burning the pulverized mixed stone at approximately 1,000° C. for about seven days to a lump; and
   repulverizing said lump.

2. The method of claim 1, said step of setting up the base, comprising the steps of:
   setting up a brazier;
   setting up a substrate of said first furnace on said brazier;
   placing a first tinfoil on said substrate; and
   layering a plurality of layers comprising layers of yellow soil, kaolin, sericite, and biomineral in sequence, on said first tinfoil, while putting a second tinfoil on each of said plurality of layers.

3. The method of claim 2, said step of setting up the substrate, comprising the step of setting up an iron railing, an iron rod and an iron plate on said brazier.

4. The method of claim 2, said step of setting up the second furnace, comprising the steps of:
   wrapping a copper plate with a third tinfoil;
   putting a fourth tinfoil on an inner surface of said second furnace and an external surface at a lower portion of said second furnace; and
   winding the external surface of said second furnace with a gas pipe connected to said biomineral layer.

5. The method of claim 2, each of said plurality of layers being 10 tons in weight.

6. The method of claim 4, wherein said gas pipe is made by winding a copper wire and the tinfoil.

7. The method of claim 2, wherein said brazier is a gas brazier.

8. The method of claim 1, a particle size of said pulverized elvan being under about 74 μm.

9. The method of claim 1, said pulverized mixed stones comprising about 40 wt % of said germanium, about 15 wt % of said tourmaline, about 30 wt % of said zeolite, and about 15 wt % of said franklinite.

10. The method of claim 1, a particle size of said pulverized mixed stone being under about 44 μm.

11. The method of claim 1, wherein a particle of the repulverized lump is as small as said particle can be passed through a number 500-mesh screen.

12. The method of claim 1, further comprising, before the step of repulverizing, the step of cooling said lump.

13. The mineral composition manufactured by the method of claim 1.

14. The mineral composition manufactured by the method of claim 9.

15. The mineral composition manufactured by the method of claim 11.

16. A method for manufacturing a mineral composition, the method comprising the steps of:
    pulverizing a mixed stone comprising germanium, tourmaline, zeolite, and franklinite; and
    heating and burning the pulverized mixed stone in a furnace loaded with elvan.

17. The method of claim 16, further comprising the step of repulverizing the burned mixed stone.

18. The mineral composition manufactured by the method of claim 16.

19. A method for manufacturing a mineral composition, comprising the steps of:
    preparing pulverized mixed stones comprising about 40 wt % of said germanium, about 15 wt % of said tourmaline, about 30 wt % of said zeolite, and about 15 wt % of said franklinite;
    heating and burning the pulverized mixed stone in a furnace loaded with elvan; and
    pulverizing the burned mixed stone.

20. The mineral composition manufactured by the method of claim 19.

* * * * *